United States Patent
Rohlfsen

(10) Patent No.: US 9,029,610 B2
(45) Date of Patent: *May 12, 2015

(54) **METHOD FOR CULTIVATION OF *MONARDA FISTULOSA***

(75) Inventor: William G. Rohlfsen, Manson City, IA (US)

(73) Assignee: Prairie Pharms, LLC, Mason City, IA (US)

( * ) Notice: Subject to any disclaimer, the term of this patent is extended or adjusted under 35 U.S.C. 154(b) by 487 days.

This patent is subject to a terminal disclaimer.

(21) Appl. No.: 13/359,045

(22) Filed: Jan. 26, 2012

(65) Prior Publication Data

US 2013/0197277 A1 Aug. 1, 2013

(51) Int. Cl.
- *C07C 37/68* (2006.01)
- *C07C 37/76* (2006.01)
- *A01D 45/00* (2006.01)
- *C07C 37/00* (2006.01)
- *A01G 1/00* (2006.01)

(52) U.S. Cl.
CPC .............. *C07C 37/004* (2013.01); *C07C 37/68* (2013.01); *C07C 37/76* (2013.01); *A01D 45/00* (2013.01); *A01G 1/001* (2013.01)

(58) Field of Classification Search
CPC ...... C07C 37/68; C07C 37/76; C07C 37/004; A01D 45/00
USPC ......................................................... 568/756
See application file for complete search history.

(56) References Cited

U.S. PATENT DOCUMENTS

| | | | |
|---|---|---|---|
| 5,591,435 A * | 1/1997 | Vaccarello-Dunkel et al. | 424/740 |
| 6,902,726 B1 * | 6/2005 | Varel | 424/76.6 |

OTHER PUBLICATIONS

Seymour et al. Six Basic Elements for a Successful Native Grass and Forb Establishment, 2008, obtained from https://www.tn.gov/twra/pdfs/nativegrass6elements.pdf.*
Keefover-Ring, K., Aquilegia, 2006, 30, pp. 3-4.*
Weaver et al. Journal of Chemical Ecology, vol. 21, 1995, 127-142.*
Mazza et al. Flavour and Fragrance Journal 1987, 2, 129-132.*
Mazza et al. Monarda: A source of geraniol, linalool, thymol and carvacrol-rich essential oils, 1993, p. 628-631. In: J. Janick and J.E. Simon (eds.), New crops. Wiley, New York.*

* cited by examiner

*Primary Examiner* — Joseph Kosack
*Assistant Examiner* — Matthew Coughlin
(74) *Attorney, Agent, or Firm* — Camille L. Urban; David M. Breiner

(57) ABSTRACT

A method for cultivating *Monarda fistulosa* includes planting seeds at rates between about 2.5 and about 5 pounds per acre, preferably about 4 pounds per acre. Fuel costs are reduced because seeding, mowing the first season, and harvesting in seasons thereafter are all that is required. Reduction in herbicide use results from the heavy rate of planting, improved germination attributed to rolling, and the plant's natural herbicides which are more highly effective when seeded at the higher rate. The method includes seeding, mowing during a first growing season, and harvesting each season thereafter. This method results in oil without weed contamination and carvacrol levels are high.

12 Claims, 4 Drawing Sheets

METHOD FOR CULTIVATION OF *MONARDA FISTULOSA*

FIELD OF INVENTION

Figure 1:
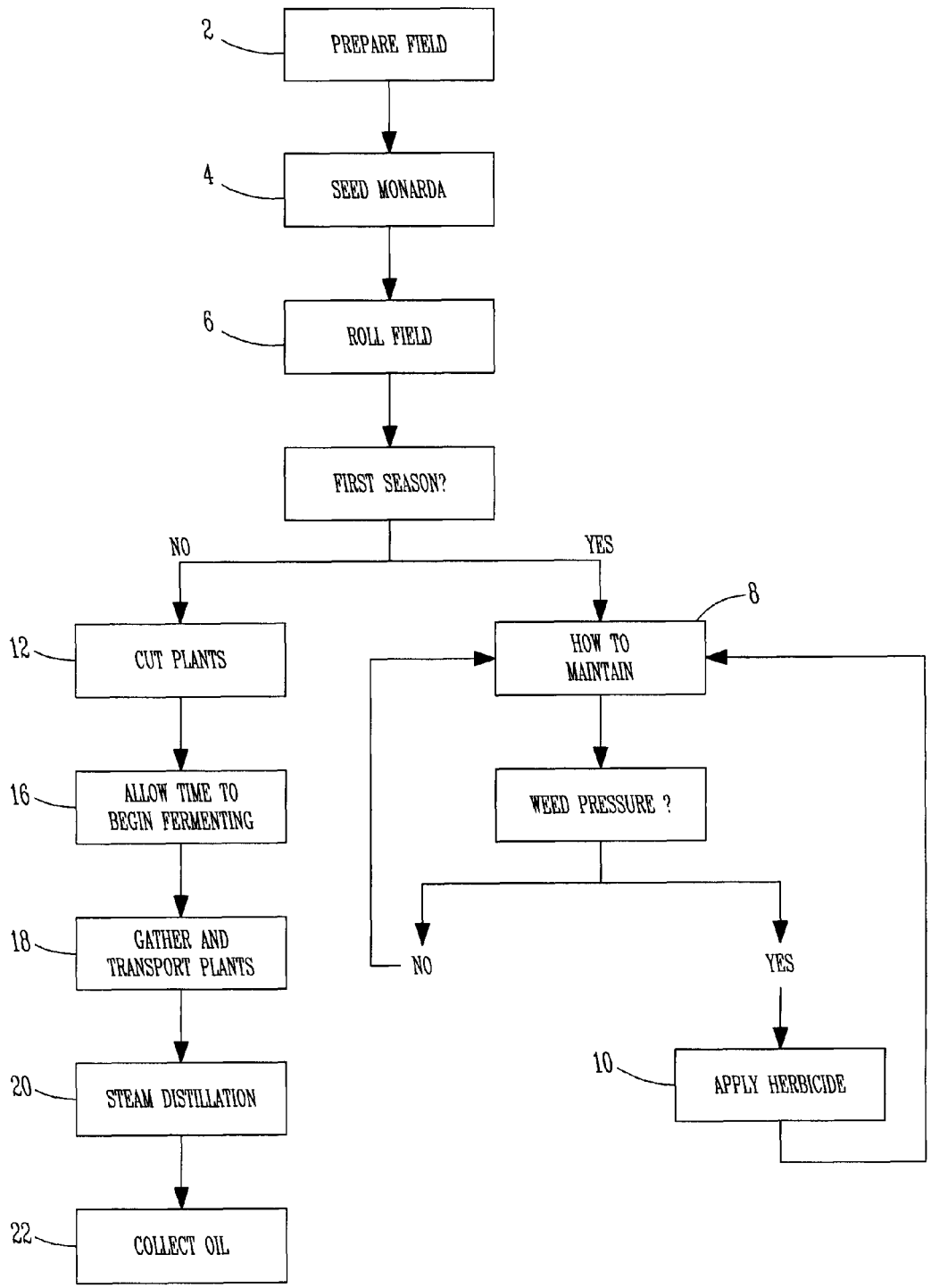

The present invention relates to a method for producing *Monarda* Fistulosa for the efficient harvest of carvacrol essential oil.

BACKGROUND

Some plant essential oils have long been known to possess properties that can be employed as food or flavoring, and for medicinal and industrial purposes. Different plant species provide different oils. For example, peppermint for the peppermint plant's leaves which provides flavoring is sometimes used as an aid for digestive issues. And clove oil is extracted from flowers and used for flavoring, scent, and various historical medicinal purposes. *Eucalyptus* oil, produced from the leaves of *Eucalyptus globulus* is used in many cleaning solutions and as an antiseptic.

As another example, *Monarda fistulosa* and many other plants belonging to the true mint family i.e. labiate, have been a source of geraniol, thymol and carvacrol essential oils. Geraniol is used in perfumes. Thymol is used in mouthwash as an antiseptic and has been shown to have antifungal activity, as well. It is known that Carvacrol may also be used as an antimicrobial, antifungal and as a flavoring.

Although it would seem likely that every plant of a species would have a similar oil content profile, it has been found instead that different races of a plant species may provide different ratios of the essential oils they produce. There are many theories as to the reasons for these differences which include response to climate, moisture levels, nutrient levels, evolution due to these pressures, etc.

Many plants are indigenous to a particular geographic area and/or climate. Historically, those who sought plant oils would gather many plants from their natural habitat. Some plants containing desirable oil have been cultivated for research purposes related to the oil. However, commercial use of *Monarda* to date includes propagation for seeds to add color to natural prairie and wildflower seed mixes.

Cultivation for research or seed purposes may include transfer of the plants from their native growth area to a different geography, climate or soil type or a combination of these. Natural travel of seeds from one area to another may also result in new habitats for a given plant wherein the new habitat may include differing climate, soil, or pests from those in the original habitat. It has been noted that such transfer may result not only indifferent physical characteristics of the plant in response to the environmental differences, but that these changes may, in turn, result in different ratios of the oils produced by the plant.

*Monarda* is a genus consisting of about 16 species. The plants are erect, herbaceous, annual or perennial plants in the family Lamiaceae and are native North America. The plants typically range in height from 1 to 3 feet (0.2 to 0.9 m), the plants have an equal spread, with slender and long-tapering (lanceolate) leaves. The leaves, when crushed, exude a spicy, highly fragrant oil. Common names include bee balm, horsemint, oswego tea, and bergamot, among others. When the term "*Monarda*" is used herein it is understood that it includes plants known by these names, as well, provided the plant meets the characteristics of the *Monarda* genus.

In the case of *Monarda fistulosa*, several studies provide information pertinent. In the early 1970's (MARSHALL H, H, and R. W. SCORA.1972. A new chemical race of *Monarda fistrrlosa* (Labiatae).Can. J. Bot. 50: 1845-1849.) a new chemical race of *Monarda fistulosa* was discovered in Manitoba Canada and studied. *Monarda fistulosa* is widely distributed throughout North America and a plant had been discovered having a different scent than most others. It was dubbed "sweet *Monarda*" due to the scent which was the only difference discernable without chemical testing. Other Sweet *Monarda* plants were then found, albeit far more scarce than the dominant type. The Sweet *Monarda* plants were generally more scarce and did not grow at many of the study's collection sites. Typically, the sweet *Monarda* plants were collected on light sand and stabilized dunes.

Sweet *Monarda* was crossed with other *Monarda*. Then the oils of the crosses and of the Sweet *Monarda* were studied using chromatography of the leaf oil. The researchers found that oil from the nonsweet *Monarda* was moderately viscous and was reported clear and colorless whereas oil from Sweet *Monarda* smelled sweet. Chromatograms showed that oil form the Sweet *Monarda* included far more geraniol but far less thymol and carvacrol than the non-sweet *Monarda* plants tested.

Another study completed in 1993 (Mazza, G., F. A. Kiehn, and H. H. Marshall. 1993. *Monarda*: A source of geraniol, linalool, thymol and carvacrol-rich essential oils. p. 628-631. In: J. Janick and J. E. Simon (eds.), New crops. Wiley, New York.) looked at *Monarda* as a source of certain oils, specifically, geraniol, linalool, thymol and carvacrol. This study also presented the idea that plants of a given species but grown and maintained in different geographical regions may yield different oils. When *Monarda fistulosa* is crossed with *M. didyma* a vigorous hybrid is produced that yields geraniol, linalool, thymol, carvacrol and other terpenes. However, multiple crosses as conducted by this study resulted in a sterile plant which had to be propagated by division. The study employed a planting rate of 10,000 plants/ha (or 24,000/acre). The study acknowledged that propagation via crown divisions would be easily achieved but, because crown division is cumbersome and inefficient, the study recommended using stem cuttings instead. The cuttings were recommended to be 10-12 cm in length with their bases dipped in rooting compound and then placed in sand in a misting chamber. Roots were reportedly produced in a week using this method and recommended to be transplanted in 14-16 days. Further, weeds were reported as being easily controlled by herbicides such as trifluralin, terbaacil, solan, and paraquat. Post harvest, hydrodistillation was employed to extract the oils which were then subjected to gas chromatography and mass spectrometry. One of the hybrids showed a high level of geraniol; this hybrid is now grown in southern Alberta, Canada for geraniol production.

Rust, otherwise known as *Puccinia menthe*, was reported as the major disease of the sterile *Monarda* (Mazza, 1993) causing defoliation, stem damage and degeneration of plants. Recommendations for control of rust include application of the herbicide paraquat in early spring. This article also reported variations of essential oil yields between about 0.65 and 1.2 g/100 g of fresh plant material or between about 60-125 kg of oil/ha.

As described earlier, Carvacrol and Thymol have both antiseptic and antimicrobial activities and have been used accordingly. It also appears that one—may be used as an herbicide of sorts, specifically, for control of moss and liverwort. Geraniol is used most often for its scent in products such as perfumes. In the present invention, it was postulated by the inventors that levels of oil in the *Monarda fistulosa* plants may be at least somewhat dependent on planting and growth methods.

Finding a dependable means of growing and harvesting oil from *Monarda fistulosa* in a manner selective for the desired oil would be beneficial.

For the most part, historically *Monarda fistulosa* has been cultivated as a seed for wildflower planting purposes rather than for oil production albeit some plants have been selected for geraniol production. *Monarda fistulosa* is an erect aromatic annual or perennial plant which bears pretty pinkish/lavender flowers. It is often used in wildflower seed mixes and in prairie restoration projects. Recommended methods for cultivation of *Monarda fistulosa* include planting rates of between about 0.25 lbs/acre and 2 lbs/acre, and cutting and or splitting the plants to increase them, etc.

What was needed was a method of producing *Monarda fistulosa* on a commercial scale and economically to produce a relatively high level of carvacrol. A desirable method of doing so would reduce cultivation expenses and labor while providing a dependable means for a reliable harvest of the multi-use oil.

It was therefore one objective of the present invention to determine appropriate seed planting rates and spacing to provide and encourage efficient production of carvacrol.

It was another objective of the present invention to provide a method of growing *Monarda fistulosa* that would result in least expense for weed and/or rust control while providing high levels of desired essential oil or oils.

It was another objective of the present invention to provide a method for cultivating *Monarda fistulosa* that reduced the amount of fuel required specifically by reducing the need for fuel used to apply herbicides, and boiler fuel used in distilling/cooking through unwanted weeds mixed in with the *Monarda*.

It was another objective of the present invention to provide a method for planting, cultivating and harvesting *Monarda fistulosa* that provided an economically viable manner of producing one or more essential oils.

It was a primary objective of the present invention to provide a method of cultivation of *Monadra fistulosa* that increased consistent results of high quality and high production levels of the desired oil.

SUMMARY OF THE INVENTION

The present invention includes a recommended planting rate and cultivation methodology that has heretofore been unknown. The method increases germination, decreases herbicide use and fuel use, and increases the yield of *Monarda fistulosa* oil. Although known recommended planting rates for *Monarda fistulosa* ranged from about 0.25 to up to 2 lbs per acre (*Monarda fistulosa* contains 1,120,000 seeds/lb) for producing seeds for use in wildflower seed mixes and prairie grasses, it was surprisingly found that these rates did not provide the better means for cultivating and harvesting the plants and the desired essential oils they contained. At the rates previously recommended, weed pressure causes a decrease in yield of oil, and causes an increase in levels of unwanted contaminants associated with those weeds (e.g. aromatic sap from the weeds) which may appear in the harvested oil. These contaminants may reduce oil quality by up to 40%. Removing these weeds from a field of *Monarda fistulosa* to avoid the contamination and downward pressure on yield, requires more fuel to be used in the operation to remove/destroy those weeds and/or herbicides. The result is a reduction in the efficiency of the overall operation.

The inventors experimented in a 12 acre field drill seeded at differing rates. Specifically, 2.0, 2.5, 3.0, 3.5, 4.0, 4.5 and 5.0 pounds of seed per acre. Photos taken 5 days prior to harvest showed a dramatic decrease in weeds at the higher rates versus those in the lower planting rates at the first harvest. Photos taken 30 days after harvest showed that the lower planting rates of *Monarda fistulosa* planting resulted in higher weed pressure even at this stage which, in turn, will translate to increased pressure the following season.

Further, it was determined that rolling the ground after either drilling or broadcast seeding increase germination. Theoretically, the soil compression provided by the roller provides a better barrier for retaining moisture and for protection against birds or other pests while the seeds germinate.

Instead, the present invention recommends planting rates ranging from about 2.5 lbs/acre to about 5 lbs/acre or, more preferably, around about 4 lbs/acre either via broadcast seeding or drilling. Further, the method includes rolling the ground securing the soil around drilled or broadcast seeds to seal in moisture. In some embodiments, the method advises no harvest the first season but, rather, regular mowing. Some embodiments provide recommended methods of weed control that are plant-population dependent, others employ herbicides or some combination of the two. Recommendations regarding pesticide use and fertilizer application are also provided. The method advocates certain practices related to harvesting *Monarda fistulosa* for best yield of the desired oil and describes means and method for separating the oil from the plant. Finally, the method includes recommended best practices for the maintenance of the perennial and number of seasons for production prior to destruction.

In short, one of the preferred embodiments includes drilling seed or broadcast seed application of between about 2.5 lbs and about 5 lbs per acre, more preferably between about 3.5 lbs and about 4.5 lbs per acre, and most preferably around 4 lbs per acre. Once applied, means to seal moisture in are employed. A recommended method is the use of a roller across the field to both compact the soil to a degree and to seal in moisture. Seeding is done in the spring of the year.

Other objects, features, and advantages of the present invention will be readily appreciated from the following description. The description makes reference to the accompanying drawings, which are provided for illustration of the preferred embodiment. However, such embodiment does not represent the full scope of the invention. The subject matter which the inventor does regard as his invention is particularly pointed out and distinctly claimed in the claims at the conclusion of this specification.

DRAWINGS

Figure 2:
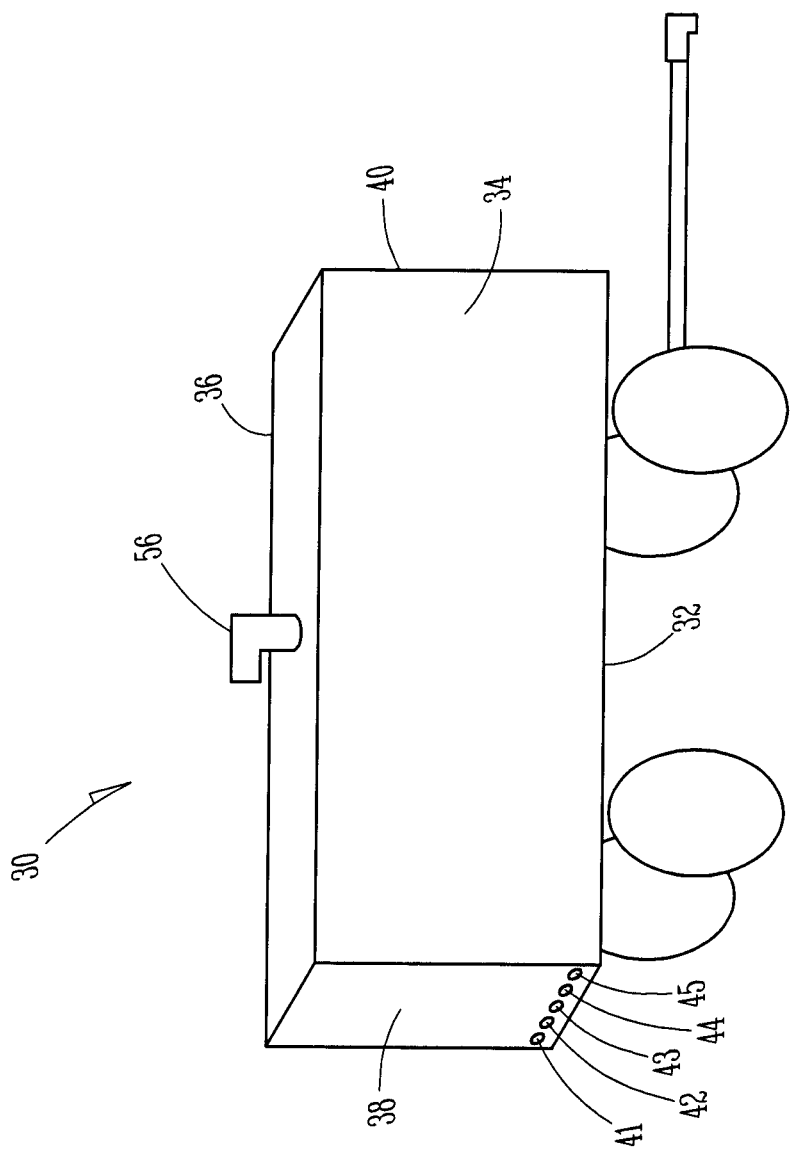
Figure 3:
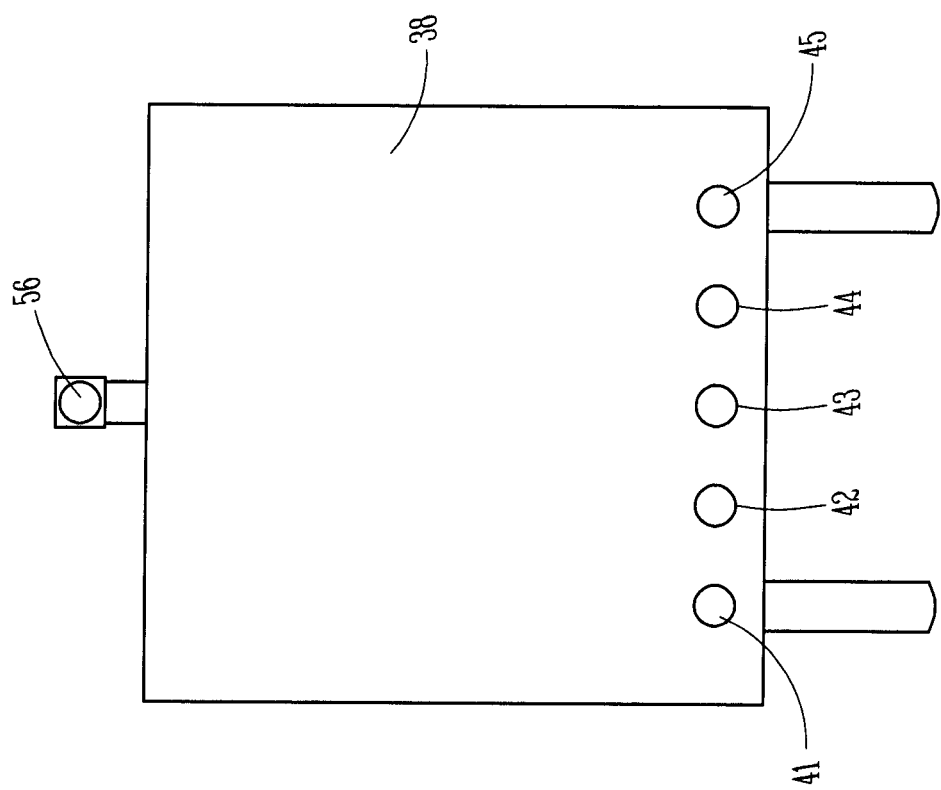
Figure 4:
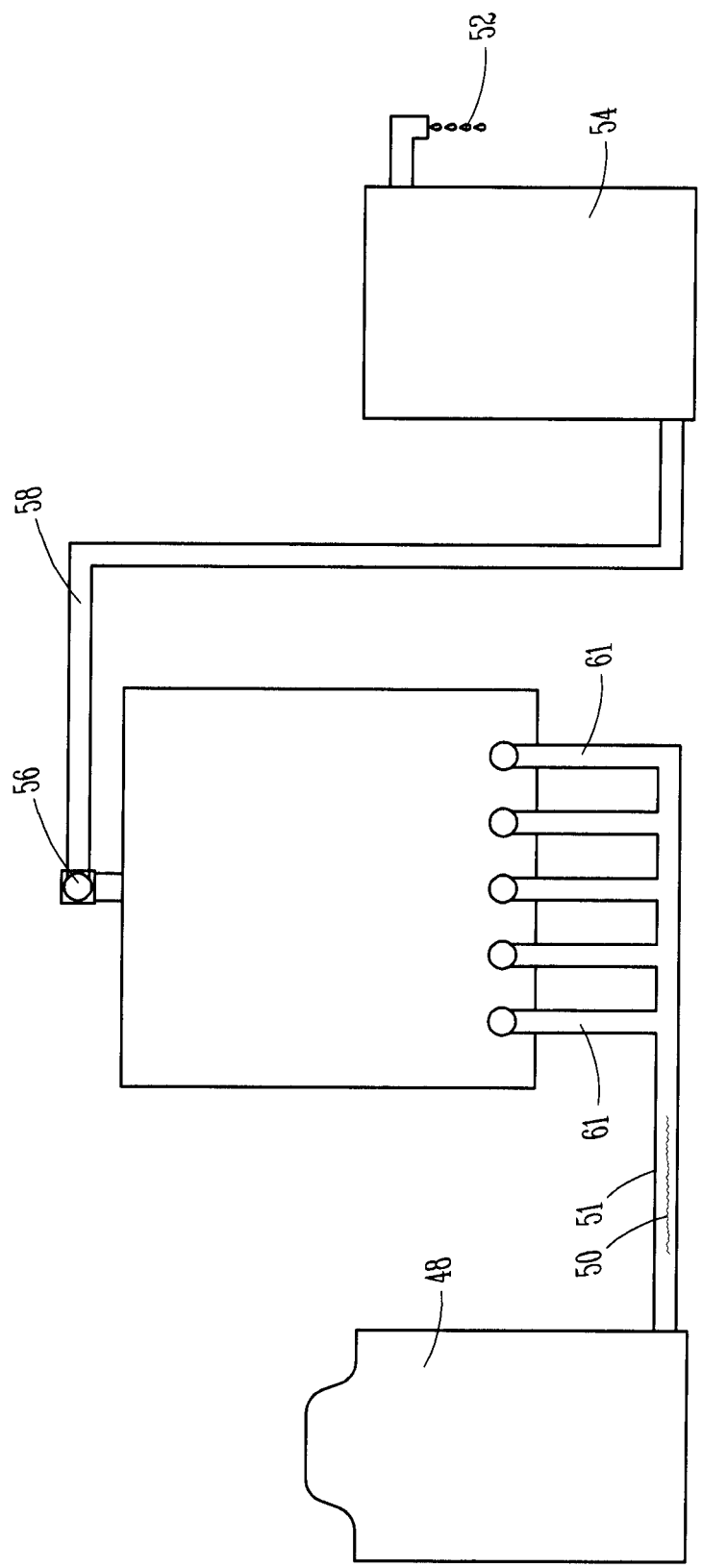

FIG. 1 flow chart describing the cultivation process;
FIG. 2 perspective view of means for transporting;
FIG. 3 end view of means for transporting; and
FIG. 4 schematic illustrating steam distillation components.

DETAILED DESCRIPTION

The present invention comprises planting seed of *Monarda fistulosa* in a field at a rate between about 2.5 lbs per acre and about 5 lbs per acre and more preferably between about 3.5 and 4.5 lbs per acre, mowing the field regularly the first year, and then harvesting it in years thereafter. The lifetime of plants 14 for a single planting is typically 5-7 harvests, but may be longer or shorter depending on soil conditions, climate and husbandry practices. The equipment used to condition the field, plant the seed, mow the plants, cut the plants, and gather the plants may each be of any type readily known and understood by one of skill in the art. Examples of each of these types of equipment are provided herein by machine producer's brand name but they are provided strictly for purposes of example, and not for limitation.

Referring now to FIG. 1 the field 12 is prepared 2 by routine tilling, field cultivating, discing or other means for turning or loosening the upper layer of soil. For example and not for limitation, a disc 16 by CaseIH, Krause, or other implement dealer may be used. Next, the field is seeded 4. Seed 10 then may be drilled or broadcast. When drilled, spacing of about 8 inches to about 10 inches is desired. Although many permissible drills exist, two examples are produced by Brillion or Taka. Alternatively, the seed 10 may be broadcast. Again, a variety of acceptable broadcasting devices are available such as a TerraGator. In either case, broadcasting or drilling, seed 10 should be planted at the rates mentioned above.

In a preferred method, planting (via drill or broadcast or other means) is preferably followed by rolling or other soil compression activities 6. An example of an acceptable roller device is a Riteway model 4300 which weighs between 15,800 lbs and 23,500 pounds. Rolling or other compression actions are preferably completed the same day as the field is cultivated and also, and more critically, within 2 to 48 hours after drilling or broadcasting seed. The timing is recommended in order to avoid overdrying the soil, protect the seeds from birds, and to compress the soil enough to create a seal to assist in retaining moisture to improve germination percentages for the seeds.

During the first season, the field 12 should be mowed 8 on a regular basis. Depending on rainfall, soil and climate conditions, mowing may be done as often as 4-6 times in a season or as infrequently as 2-4 times. Weeds grow much faster in the first season than does the Monarda, so mowing is aimed to keep the weed height reduced to allow the Mondarda to become established. Mowing should be done to maintain the field between about 8 and 10 inches and, more preferably when they are about 8 inches tall, as many times in the first season as needed to keep the plants less than about 8 to 10 inches high. At the end of the first growing season, the plants are left around 8 inches tall to catch snowfall. Any suitable mowing machine 24 may be employed. For example, several models of the Woods bat-wing mower work well.

It is foreseeable that seeds 10 planted in a bare field 12 the first season where ground cover or crop previously existed may be subjected to some weed pressure early in the growing season. When this occurs, application of Assure II or Select Max work well. Other herbicides applications 10 also likely to be effective, however, broadleaf herbicides may not be used because they damage Monarda.

The second growing season is unlikely to require any herbicides, however, Assure II, Basagram and SelectMax are but a few examples of herbicides that may be employed if needed. Due to the planting rate, the compression of the soil, and multiple mowings in the first season, plants will emerge early and tend to grow quickly. Monarda fistulosa plants 14 produce their own herbicidal chemicals one of which is carvacrol. These chemicals act to control any weeds that are not simply physically crowded out by the Monarda. The action of the carvacrol effects germination of the weed seeds. The planting rate, the growth rate, the size of the plants, and the Mondarda's own chemical defenses result in a crop that typically requires no further herbicide treatments but for, perhaps, an occasional weed patch which may be controlled via hand sprayer or physical removal. In midsummer, Monarda fistulosa plants produce a lavender colored fragrant flower. The plants are harvested at flower peak which, in the Midwest, is generally early to mid July.

Harvest of Monarda fistulosa fields cultivated in the manner of the present invention may be accomplished in several ways using various equipment. A preferred method is to employ is a MacDon draper or any other cutting machine to cut 12 the plants 14 with flowers attached and leave them lay where they were cut. The cut plants should remain in the field for 2-8 hours, preferably 2-6 hours and more preferably 4-6 hours 16. It is best, but not critical, that these hours be warm and sunny. Leaving the plants lay starts the process of oil release from the inter cellular pockets within the plant. The cut plants 14 are then gathered by a suitable device such as a forage chopper 18 and placed in means to transport 30 them from the field.

In one embodiment, means to transport 30 the cut plants 14 comprises a generally watertight wagon having a floor 32, two sides 34, 36, and two ends 38 and 40 with multiple ports 41-45 near the floor 32 in one of the ends 38 or 40 The wagon 30 just described is used in one of several methods for removing oil from Monarda fistulosa, specifically steam distillation.

Steam distillation of oil from plants is old in the art and works on the principle that steaming the cut plants encourages release of the plants' essential oils via rupture of the plant's oil sacs which are taken up with the steam. During steam distillation 20 a boiler 48 creates steam 50. The steam 50 travels through a conduit 51 to said means to transport 30 and enters through ports 41-45 near the floor 32. The steam travels upward and with oil 52 is removed through the port 56 into a second conduit 58. The steam 50 and oil 52 is run through a condenser 54 which causes the oil 52 and water in the steam 50 to separate allowing the oil 52 to be recovered 22. When using the wagon 30, a steam input 61 is connected to each port 41-45. Steam is injected into the wagon and, as it travels upwards, oil 52 from the plants 14 is removed with the steam. The steam and oil then exit the top of the wagon through the port 56 and flow into or through one of many different kinds of condensers 60 where the oil 52 is recovered and the condensed steam (water) may be reheated and reused in the process.

The method of cultivation just described increases germination, decreases herbicide use and fuel use, and increases the yield of Monarda fistulosa oil. Oil yield from various methods of cultivation are presented on Table 1. Further, the above-mentioned cultivation method results in oil content that is commercially desirable, namely, increased amounts of carvacrol. Although known recommended planting rates for Monarda fistulosa ranged from about 0.25 to up to 2 lbs per acre (Monarda fistulosa contains 1,120,000 seeds/lb), it was surprisingly found that these rates did not provide the better means for cultivating and harvesting the plants and the desired essential oils they contained. Oil quality is high at least partially due to the reduction and near elimination of weed pressure and its resulting contamination.

Thus, the present invention has been described in an illustrative manner. It is to be understood that the terminology that has been used is intended to be in the nature of words of description rather than of limitation.

Many modifications and variations of the present invention are possible in light of the above teachings. For example, distillation may be accomplished in other ways; seeds may be planted via hand, or via traditional planters, or other seed planting devices not yet known. New effective herbicides may become known. New Monarda hybrids may be developed and it may be determined that other mans may be employed to increase oil production even more, specifically the level of carvacrol in the Monarda. Therefore, within the scope of the appended claims, the present invention may be practiced otherwise than as specifically described.

What I claim is:

1. A method for cultivating *Monarda fistulosa* said method comprising increasing the yield of essential oils produced by the *Monarda fistulosa* by preparing a field for planting seed, planting seed with a broadcast seeding device at a rate of greater than 3.0 pounds per acre to about 5 pounds per acre, and harvesting plants grown from the seeds from said field wherein the essential oils produced include carvacrol.

2. The method of claim 1 further comprising using a soil compression device after seeding for at least partially sealing in moisture.

3. The method of claim 1 further comprising a plurality of seasons wherein plants are mowed at least once without harvesting during a first growing season, and harvested after each of the remaining plurality of growing seasons.

4. The method of claim 1 wherein the yield of essential oils comprise at least 70% carvacrol and less than 5% thymol.

5. The method of claim 1 wherein the yield of said essential oils comprises at least about 70% carvacrol.

6. The method of claim 1 wherein harvesting plants comprises cutting the plants, allowing plants to lay in the field for a plurality of hours, gathering plants, and separating said oils from said plants by steam distillation.

7. The method of claim 1 wherein the quality of said essential oils is improved by reducing the level of contamination by material from weeds.

8. The method of claim 6 wherein said plurality of hours comprises a range between about 2 hours and about 6 hours.

9. A method for cultivating *Monarda fistulosa* to increase yield of essential oils produced by the *Monarda fistulosa* comprising preparing a field for planting seed, planting seed of *Monarda fistulosa* with a drill seeding device at a rate of greater than 3.0 pounds per acre to about 5 pounds per acre, and harvesting plants grown from the seeds from said field.

10. The method of claim 9 wherein said at essential oils comprises carvacrol present at a level of at least about 70%.

11. A method for cultivating *Monarda fistulosa* to increase a per acre volume of essential oils harvested from said *Monarda fistulosa*, said volume of essential oils comprising at least about 70% carvacrol, said method comprising planting seed of *Monarda fistulosa* at a rate of between about 3.5 pounds and about 5 pounds per acre to grow *Monarda fistulosa* plants and separating said essential oils from said plants.

12. The method of claim 1 wherein the yield of carvacrol is at least about six gallons per acre.

* * * * *